(12) United States Patent
Ishiwatari

(10) Patent No.: US 6,327,813 B1
(45) Date of Patent: *Dec. 11, 2001

(54) INSECT CONTROLLER

(75) Inventor: Takao Ishiwatari, Toyonaka (JP)

(73) Assignee: Sumitomo Chemical Company, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/917,960

(22) Filed: Aug. 27, 1997

(51) Int. Cl.[7] .................................................. A01M 13/00

(52) U.S. Cl. ............................................................ 43/125

(58) Field of Search ........................... 43/1, 125; 239/54, 239/55, 60; D22/120, 119, 123, 125; 422/305

(56) References Cited

U.S. PATENT DOCUMENTS

| | | | | |
|---|---|---|---|---|
| 274,425 | * | 3/1883 | Wells | 239/54 |
| 2,120,204 | * | 6/1938 | Langhorst | 239/54 |
| 2,674,018 | * | 4/1954 | Crippen | 43/125 |
| 3,027,678 | * | 4/1962 | Whitney | 43/125 |
| 3,823,873 | * | 7/1974 | Miller | 239/54 |
| 4,597,218 | * | 7/1986 | Friemel | 43/125 |

* cited by examiner

Primary Examiner—Kurt Rowan
(74) Attorney, Agent, or Firm—Birch, Stewart, Kolasch & Birch, LLP

(57) ABSTRACT

An insect controller in which at least one volatile insecticidal or insect repellent compound that volatizes without heating is carried on a support with at least one through hole. The use of a volatile insecticidal or insect repellent compound without heating can ensure satisfactory insect-controlling effects. If a specific structure, e.g., folding structure, is employed for the insect controller, wasteful evaporation of the volatile insecticidal or insect repellent compound can be reduced during non-use.

7 Claims, 2 Drawing Sheets

INSECT CONTROLLER

FIELD OF INVENTION

The present invention relates to an insect controller and more particularly to a controller for killing or repelling harmful insects. The present invention provides a simple means of controlling harmful insects without heating, unlike the conventional mosquito coils, electric mosquito mats and devices having an insecticidal liquid and a wick wherein the lower part of the wick is immersed in the insecticidal liquid and the upper part of the wick is heated with an electric heater. Among the insect controllers of the present invention are those which can be used as interior ornaments.

SUMMARY OF THE INVENTION

The present invention provides an insect controller comprising a volatile insecticidal or insect repellent compound without heating, which is carried on a support with at least one through hole.

DETAILED DESCRIPTION OF THE INVENTION

The insect controller of the present invention comprises a volatile insecticidal or insect repellent compound volatilized without heating, which is carried on a support with at least one through hole.

For the volatile insecticidal or insect repellent compound volatilized without heating, which is used in the present invention, the vapor pressure at 20° C. is preferably $1.0 \times 10^{-4}$ mmHg or higher. Typical examples of the volatile insecticidal or insect repellent compound include pyrethroid compounds which are volatile without heating, such as empenthrin, transferring and 1-ethynyl-2-fluoro-2-pentenyl 3-(2,2-dichlorovinyl)-2,2-dimethylcyclopropanecarboxylate, as well as insect repellent compounds which are volatile without heating, such as carane-3,4-diol, N,N-diethyl-m-toluamide and 1-methyl-n-propyl 2-(2-hydroxyethyl)-1-piperidinecarboxylate, which have a vapor pressure at 20° C. ranging from $1.0 \times 10^{-4}$ mmHg to $5.0 \times 10^{2}$ mmHg.

The support used in the present invention may have any shape, so long as it is provided with at least one through hole to ensure effective ventilation. It is preferred that the support has plural through holes. The preferred shape of the support has a ratio of surface area to volume ranging from 1 to 20 $cm^{-1}$.

The term "surface area" as used herein refers to the total area of outside and inside surfaces of a support, which are exposed to the air. The term "volume" as used herein refers to the volume determined by the external contour of a support.

Figure 1:
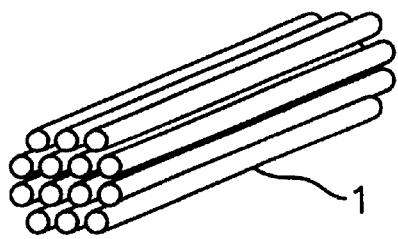
FIG. 1 is a perspective view of an insect controller of the present invention.
Figure 2:
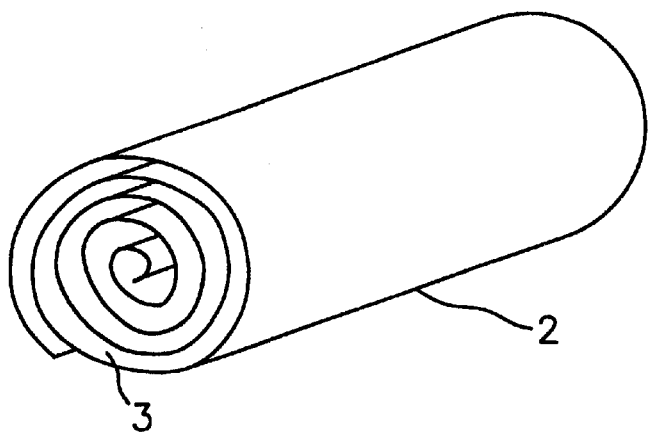
FIG. 2 is a perspective view of another insect controller of the present invention.
Figure 3A:
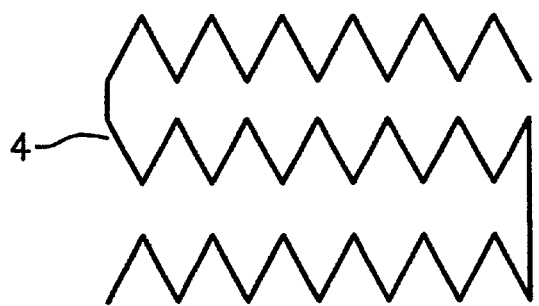
FIGS. 3a and 3b are a sectional view and a side view, respectively, of still another insect controller of the present invention.
Figure 3B:
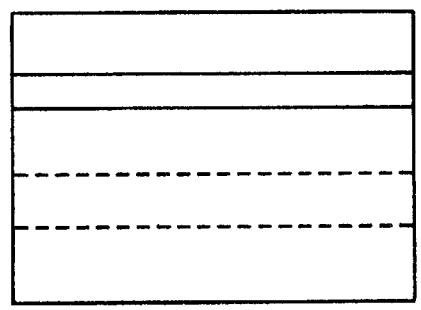

Typical examples of the support shape include a bundle of cylindrical tubes 1 as shown in FIG. 1; a roll shape 2 with a spacing 3 as shown in FIG. 2; and a folded paper shape 4 as shown in FIG. 3.

The preferred shape of the support used in the present invention may have a folding structure with plural through holes.

Figure 4A:
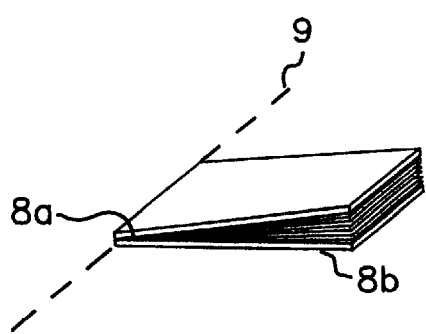
FIGS. 4a and 4b are perspective views of still another insect controller of the present invention. In the insect controller, the support folded as shown in FIG. 4a can be unfolded by rotation of plane members in opposite directions around a fixed axis on a side edge of the plane members, for example, at an angle of 180° as shown in FIG. 4b, which represents a form of the insect controller during use.
Figure 4B:
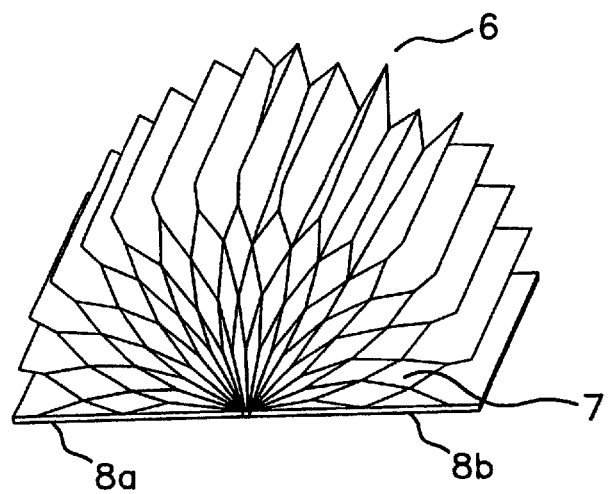

Typical examples of such a preferred shape of the support include a shape as shown in FIGS. 4a and 4b, which is well known as a paper toy (commonly called "Denguri" among the wholesale toy stores in the Osaka city). In this shape, a paper support 6 having a honeycomb structure with tubular through holes 7 is sandwiched between plane members 8a, 8b which can be unfolded or folded by rotation of the plane members in opposite directions around a fixed axis on a plane 9 or a side edge of the plane members at an angle of from 0° to 360°.

Figure 5A:
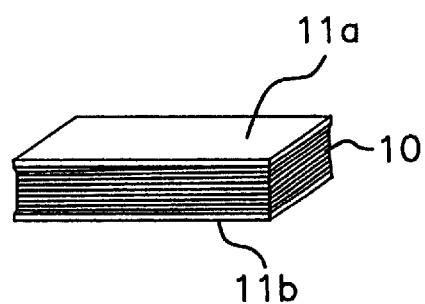
FIGS. 5a and 5b are perspective views of still another insect controller of the present invention. In the insect controller, the support folded as shown in FIG. 5a can be unfolded by parallel separation of plane members in opposite directions as shown in FIG. 5b.
Figure 5B:
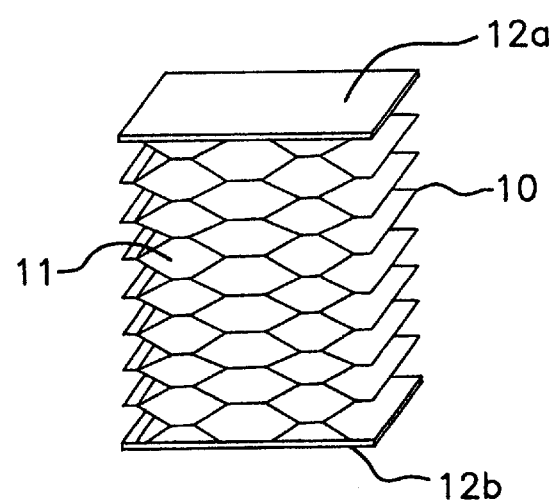

Another example of the insect controller of the present invention is shown in FIGS. 5a and 5b. In the insect controller, a paper support 10 having a honeycomb structure with tubular through holes 11 is sandwiched between plane members 12a, 12b which can be folded or unfolded by parallel movement of the plane members in opposite directions (i.e., by approach or separation of the plane members).

In the insect controller having a pair of plane members as shown in FIGS. 4a, 4b, 5a and 5b according to the present invention, the plane members are usually made of thick paper, resins or other materials.

The support used in the present invention may be made of resin films such as polyethylene and polyvinyl chloride, paper, cloths or other materials. In the case of a paper support, the use of relatively soft paper is preferred in view of easy fabrication and impregnation of an insecticidal or insect repellent compound.

The insect controller of the present invention may usually have a volume of from about 200 to about 10000 $cm^{3}$. It can be adapted for use as an interior ornament by application of appropriate patterns, colors and other features.

For the support 6,10 with plural through holes 7,11 it may preferably have about ten to about thousand through holes each having a vertical cross-sectional area of from about 0.5 to about 10 $cm^{2}$.

In an insect controller having a support with plural through holes according to the present invention, there is no need to ensure that these through holes are of the same size. It can be adapted for use as an interior ornament by combination of through holes of different sizes, or by application of appropriate patterns, colors or other features.

The amount of volatile insecticidal or insect repellent compound without heating, which is carried on the support, may vary with the kind of compound employed, the circumstances of use and the number of insect controllers applied. However, in general, satisfactory results are obtained when the volatile insecticidal or insect repellent compound is carried in an amount of from about 0.1 to about 100 g on the support in each insect controller.

The insect controller of the present invention can be used for the control of mosquitoes, flies and other harmful insects by disposing one to several controllers at an appropriate place or places in the inside of a building such as dwelling houses, offices or warehouses, or by disposing a still greater number of controllers in wider space.

In the case of an insect controller of the folding type according to the present invention, it is usually put into an unfolded state and then disposed at a desired place. When an insect controller of the folding type according to the present invention is used, the evaporation of the volatile insecticidal or insect repellent compound can be adjusted by changing the angle or degree of support unfolding.

During non-use of the insect controller of the present invention, wasteful evaporation of an insecticidal or insect repellent compound can be reduced by folding the support of the insect controller, which makes it possible to keep the insect-controlling effects for a prolonged period of time.

EXAMPLES

The present invention will be further illustrated by the following examples; however, the present invention is not limited to these examples.

Example 1

First, 20 ml of 5% (w/v) solution of 1-ethynyl-2-fluoro-2-pentenyl 1R-trans-3-(2,2-dichlorovinyl)-2,2-dimethylcyclopropanecarboxylate in acetone was uniformly applied to thirty-two cylindrical tubes made of filter paper each having a diameter of 2 cm and a length of 6.5 cm, followed by drying. These cylindrical tubes were bundled with a string so that the vertical cross-sectional contour became a rough circle as shown in FIG. 1, which afforded an insect controller of the present invention. The ratio of surface area to volume of the insect controller was about 3.0 $cm^{-1}$.

Example 2

An insect controller of the present invention was obtained in the same manner as described in Example 1, except that a 20% (w/v) solution of 1S,3S,4S,6R-carane-3,4-diol in acetone was used in place of the 5% (w/v) solution of 1-ethynyl-2-fluoro-2-pentenyl 1R-trans-3-(2,2-dichlorovinyl)-2,2-dimethylcyclopropanecarboxylate in acetone.

The preparation of an insect controller used for comparison in the following Test Example (Example 3) is described as Reference Example 1.

Reference Example 1

First, 20 ml of 5% (w/v) solution of 1-ethynyl-2-fluoro-2-pentenyl 1R-trans-3-(2,2-dichlorovinyl)-2,2-dimethylcyclopropanecarboxylate in acetone was uniformly applied to one cylindrical tube made of filter paper having a diameter of 13 cm and a height of 6.5 cm, followed by drying, which afforded an insect controller for comparison. The ratio of surface area to volume of the insect controller was about 0.62 $cm^{-1}$.

Example 3

At the center of a test room of 28 $m^3$ in size (4.3 m×2.65 m×2.45 m in height), the insect controller obtained Example 1 or Reference Example 1 was hung so that the bottom thereof was located at a height of 1.2 m from the floor. At the position horizontally 60 cm or 180 cm far from the insect controller, two nylon cages (cylindrical shape having a diameter of 30 cm and a height of 20 cm) for each distance, i.e., four nylon cages in total, each containing 20 female adults of common mosquito (*Culex pipiens pallens*) were hung so that the bottoms thereof were located at a height of 60 cm from the floor.

After 60 minutes, the number of mosquitoes knocked down was counted, and the knockdown rate (%) was determined.

During the test, an electric fan was placed directly below the insect controller to stir the air in the room, and a board was provided at the upper part of the electric fan so that the wind from the electric fan did not blow directly against the insect controller.

The results are shown in Table 1.

TABLE 1

|  | Knockdown rate (%) |
| --- | --- |
| Insect controller of Example 1 | 100 |
| Insect controller of Reference Example 1 | 0 |

Example 4

The same test as described in Example 3 was carried out by replacing female adults of *Culex pipiens pallens* by those of *Aedes aegypti.*, and the knockdown rate (%) was determined after 30 minutes.

The results are shown in Table 2.

TABLE 2

|  | Knockdown rate (%) |
| --- | --- |
| Insect controller of Example 1 | 97.1 |
| Insect controller of Reference Example 1 | 16.4 |

Example 5

First, 10 ml of 10% (w/v) solution of 1-ethynyl-2-fluoro-2-pentenyl 1R-trans-3-(2,2-dichlorovinyl)-2,2-dimethylcyclopropanecarboxylate in acetone was applied to paper for impregnation, followed by air drying. The impregnated paper was used, together with a pair of plane members each having a rectangular shape of 7.3 cm×6.5 cm in size, to prepare an insect controller having a shape as shown FIGS. 4a and 4b, in which a paper support having a honeycomb structure with tubular through holes is sandwiched between the place members. The insect controller has twenty pleats provided between the plane members so that it can be unfolded around a fixed axis on a side edge having a length of 6.5 cm at an angle of from 0° to 360°. The following test was carried out using the insect controller.

At the center of a test room of 28 $m^3$ (4.3 m×2.65 m×2.45 m in height), the insect controller obtained above was hung so that it was unfolded around a fixed axis on a side edge having a length of 6.5 cm at an angle of 360° and the bottom thereof was located at a height of 1.2 m from the floor. At the position horizontally 60 cm or 180 cm far from the insect controller, two nylon cages (cylindrical shape having a diameter of 30 cm and a height of 20 cm) for each distance, i.e., four nylon cages in total, each containing 20 female adults of common mosquito (*Culex pipiens pallens*) were hung so that the bottoms thereof were located at a height of 60 cm from the floor.

After 60 minutes, the number of mosquitoes knocked down was counted, and the knockdown rate (%) was determined to be 100%.

Example 6

The same test as described in Example 5 was carried out by replacing female adults of *Culex pipiens pallens* by those of *Aedes aegypti*.

As a result, the knockdown rate (%) after 60 minutes was determined to be 100%.

Example 7

An insect controller having a shape as shown in FIGS. 4*a* and 4*b* was prepared in the same manner as described in Example 5, except that the concentration of 1-ethynyl-2-fluoro-2-pentenyl 1R-trans-3-(2,2-dichlorovinyl)-2,2-dimethylcyclopropane-carboxylate in acetone was changed from 10% to 20%. The following test was carried out using the insect controller thus obtained.

Within a draft chamber in the laboratory having a room temperature of about 25° C. and a humidity of from 50% to 60%, the insect controller obtained above was stored in the maximum unfolded state for 3 weeks (i.e., 504 hours). After the storage, the insect controller was used for the same tests as described in Examples 5 and 6.

As a result, the knockdown rate (%) after 60 minutes was 99% for *Culex pipiens pallens* and 100% for *Aedes aegypti*.

Example 8

First, 10 ml of 20% (w/v) solution of 1S,3S,4S,6R-carane-3,4-diol in acetone was applied to paper for impregnation, followed by air drying. The impregnated paper was used, together with a pair of plane members, to prepare an insect controller having a shape as shown in FIGS. 4*a* and 4*b*.

What is claimed is:

1. An insect controller comprising a volatile insecticidal or insect repellant used without heating, which is carried on a support with a plurality of through holes, wherein the support further comprises a pair of plane members between which the support is sandwiched so that the support can be folded or unfolded by rotation of the plane members in opposite directions around a fixed axis on a plane or a side edge of the plane members, wherein the support has a ratio of surface area to volume ranging from 1 to 20 $cm^{-1}$, wherein the support is made of paper and has a honeycomb structure with polygonal through holes, and wherein the honeycomb structure is formed when the insect controller is open.

2. An insect controller according to claim 1, wherein the vapor pressure of the volatile insecticidal or insect repellent compound at 20° C. is $1.0 \times 10^{-4}$ mmHg or higher.

3. An insect controller according to claim 1, wherein the volatile insecticidal or insect repellent compound without heating is at least one selected from the group consisting of empenthrin, transfluthrin, 1-ethynyl-2-fluoro-2-pentenyl 3-(2,2-dichlorovinyl)-2,2-dimethylcyclopropanecarboxylate, carane-3,4-diol, N,N-diethyl-m-toluamide and 1-methyl-n-propyl 2-(2-hydroxyethyl)-1-piperidinecarboxylate.

4. A method for controlling harmful insects, comprising putting an insect controller as set forth in claim 1 into such a state that the volatile insecticidal or insect repellent compound evaporates without heating, and then disposing the insect controller at a place where insect controlling effects are required, wherein wind does not blow directly against the insect controller.

5. An insect controller comprising a volatile insecticidal or insect repellant used without heating, which is carried on a support with a plurality of through holes, wherein the support further comprises a pair of plane members between which the support is sandwiched so that the support can be folded or unfolded by parallel movement of the plane members in the opposite direction, wherein the support has a ratio of surface area to volume ranging from 1 to 20 $cm^{-1}$, wherein the support is made of paper and has a honeycomb structure with polygonal through holes, and wherein the honeycomb structure is formed when the insect controller is open.

6. An insect controller according to claim 5, wherein the volatile insecticidal or insect repellant compound used without heating is at least one selected from the group consisting of empenthrin, transfluthrin, 1-ethynyl-2-fluoro-2-pentenyl 3-(2,2-dichlorovinyl)-2,2-dimethylcyclopropanecarboxylate, carane-3,4-diol, N,N-diethyl-m-toluamide and 1-methyl-n-propyl 2-(2-hydroxyethyl)-1-piperidinecarboxylate.

7. A method of controlling insects by using an insect controller comprising support with a pair of plane members between which the support is sandwiched, comprising a steps of:

unfolding the support by moving the plane members in opposite directions; and volatilizing an insect repellent located on the support without heating;

wherein the support comprises a plurality of through holes, wherein the support has a ratio of surface area to volume ranging from 1 to 20 $cm^{-1}$, wherein the support is made of paper and has a honeycomb structure with polygonal through holes, and wherein the honeycomb structure is formed when the insect controller is open.

* * * * *